United States Patent [19]
Barbee, Sr.

[11] Patent Number: 5,597,189
[45] Date of Patent: Jan. 28, 1997

[54] PROSTHETIC UTENSIL AND TOOL HOLDING DEVICE FOR BOTH THE RIGHT HAND AND LEFT HAND

[76] Inventor: Gary W. Barbee, Sr., 707 Rolling Ridge, Duncanville, Tex. 75116

[21] Appl. No.: 233,262

[22] Filed: Apr. 26, 1994

[51] Int. Cl.⁶ .................. A46B 5/02; A61F 2/54; A45F 5/00
[52] U.S. Cl. .............. 294/25; 623/65; 224/218
[58] Field of Search ................ 623/65; 294/25; 401/8; 224/218, 219; 30/298; 24/306, 442, 302

[56] References Cited

U.S. PATENT DOCUMENTS

| | | | |
|---|---|---|---|
| D. 270,945 | 10/1983 | Kohn | D24/34 |
| 1,689,787 | 3/1927 | Kupferschmid | 294/25 |
| 3,752,524 | 8/1973 | Reick, Jr. | 294/25 |
| 3,942,194 | 3/1976 | Winter | 623/65 |
| 4,035,865 | 7/1977 | McRae | 16/114 R |
| 4,165,896 | 8/1979 | Hunt | 294/25 |
| 4,261,608 | 4/1981 | Bradshaw | 294/25 |
| 4,325,187 | 4/1982 | Wasson | 30/327 |
| 4,511,272 | 4/1985 | Brown | 401/6 |
| 4,602,885 | 7/1986 | Bischoff et al. | 401/6 |
| 4,606,484 | 8/1986 | Winter et al. | 224/218 |
| 4,683,620 | 8/1987 | Valsecchi et al. | 24/71 SK |
| 4,821,417 | 4/1989 | Levine | 30/298 |
| 4,944,766 | 7/1990 | Williams | 623/65 |
| 4,957,442 | 9/1990 | Prater | 434/166 |
| 5,222,986 | 7/1993 | Wright | 623/64 |

FOREIGN PATENT DOCUMENTS

| | | | |
|---|---|---|---|
| 2687097 | 8/1993 | France | 401/8 |
| 823913 | 12/1951 | Germany | 623/65 |
| 195751 | 4/1923 | United Kingdom | 623/65 |

Primary Examiner—David Isabella
Assistant Examiner—Laura Fossum
Attorney, Agent, or Firm—Derek R. Van Gilder

[57] ABSTRACT

A Prosthetic Utensil and Tool Holding Device for the manually disabled, having an elongated rigid adjustable band that is disposed around a disabled hand. A first hook and loop gripping band is further fixed to the clasp bar in a suitable manner wherein an eating utensil or tool is suitably fixed to a prehensile tool hook and a hook and loop gripping pad is suitably fixed to the first hook and loop gripping pad thereby allowing a manually disabled person to use an eating utensil or tool.

2 Claims, 7 Drawing Sheets

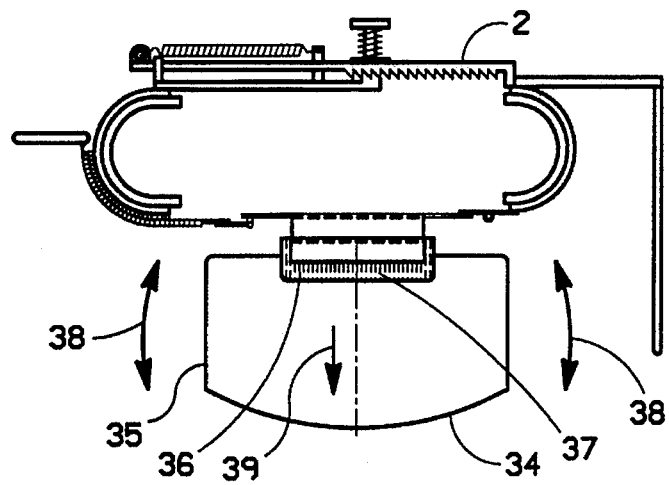
FIGURE 3
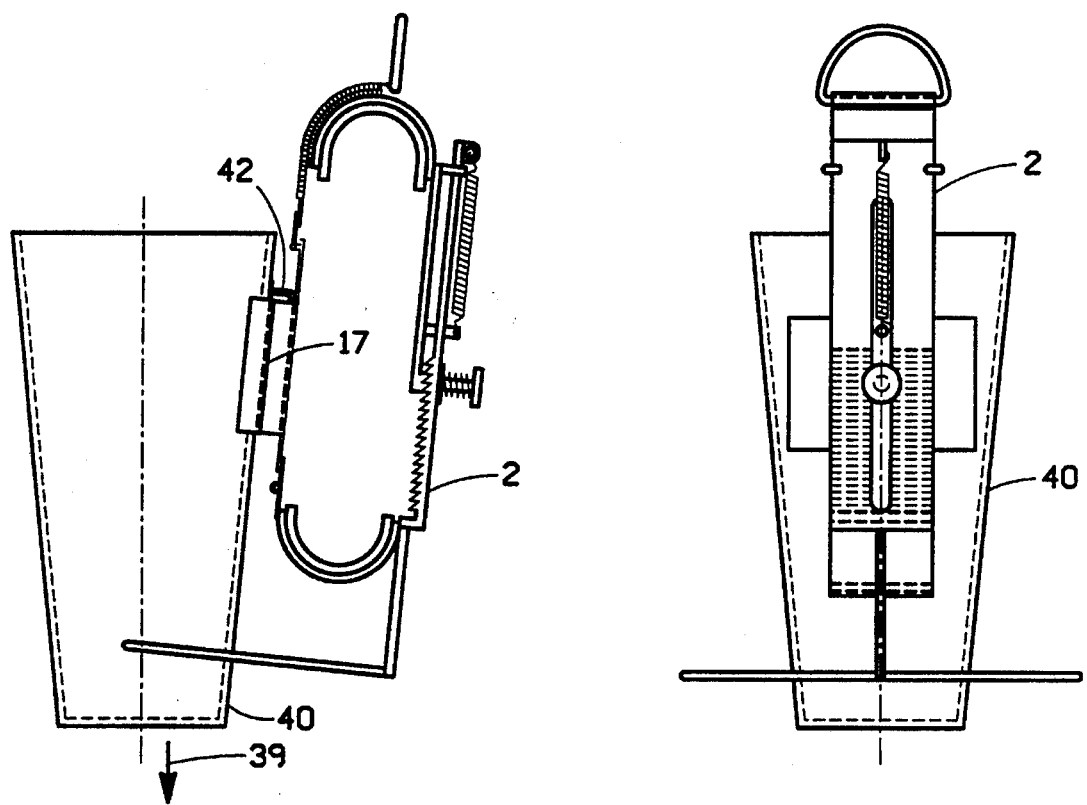
FIGURE 4
FIGURE 5

5,597,189

PROSTHETIC UTENSIL AND TOOL HOLDING DEVICE FOR BOTH THE RIGHT HAND AND LEFT HAND

BACKGROUND OF THE INVENTION

There are many hand prosthesis for grasping objects, gripping devices, holding cuffs and utensil holders for the disabled. Some of the typical designs for people with disabled hands or fingers are D. M. Wright, U.S. Pat. No. 5,222,986; S. V. Prater, U.S. Pat. No. 4,957,442; B. R. Williams, U.S. Pat. No. 4,944,766; A. H. Levine, U.S. Pat. No. 4,821,417; S. S. Bischoff, et al, U.S. Pat. No. 4,602,885; V. W. Brown, U.S. Pat. No. 4,511,272; P. E. Watson, U.S. Pat. No. 4,325,187; M. V. Bradshaw, U.S. Pat. No. 4,261,608; L. T. McRae, et al, U.S. Pat. No. 4,035,865; S. B. A Winter, U.S. Pat. No. 3,942,194; and I. Kohn, U.S. Patent No. D 270,945.

This invention is directed to a better prosthetic device and has as its principle object to be more versatile, adjustable and interchangeable.

SUMMARY

It is the object of the present invention to provide a universal prosthetic device that will efficiently operate on the right hand or left hand.

It is still another object of the present invention to provide a universal prosthetic device that can easily be adjusted to fit any hand size or four finger size.

It is yet another object of the present invention to provide a universal prosthetic device that will stand on its own to allow ease of entry of the fingers or hand into the device.

It is still yet another object of the present invention to provide a device that will allow a disabled hand to be used to independently pick up an eating utensil, a tool, or another object.

The foregoing and other objects and advantages are attained with a prosthetic utensil and tool holding device comprised of an elongated rigid adjustable band, a first hook and loop gripping band, a tool or eating utensil, a prehensile tool hook and a hook and loop gripping pad. The assembly is used to secure a utensil or tool to a disabled hand or fingers.

The features of the present invention can best be understood together with further objects and advantages by reference to the following descriptions taken in conjunction with the accompanying drawings wherein like numerals indicate like parts.

BRIEF DESCRIPTION OF THE DRAWINGS:

FIG. 3 is an elevation view showing the device secured to a knife.

FIG. 4 is an elevation of a cup secured to the device.

FIG. 5 is another elevation of a cup secured to the device.

DETAILED DESCRIPTION OF THE PREFERRED EMBODIMENT

Figure 1:
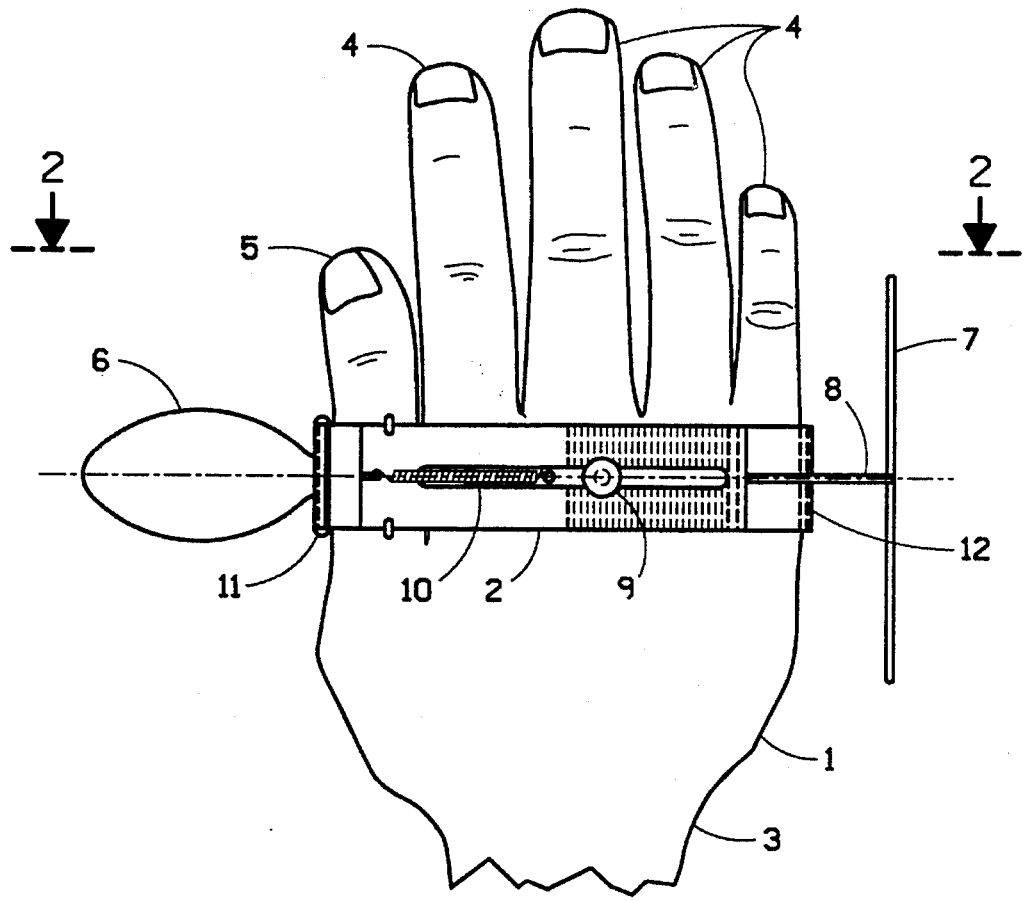
FIG. 1 is a plan view of a hand in the device.

Referring to FIG. 1 there is shown a plan view of a human hand 1 disposed in an elongated device 2. Although the elongated device 2 is shown near the wrist 3 of the hand 1 it would also be fit over the fingers 4 and thumb 5. However, if some fingers 4 or thumb 5 are severed from the hand 1, the device 2 would be placed even nearer to the wrist 3.

A spoon 6 is shown extending from the first end of the elongated device 2 that is suitably fixed around the hand 1 or the fingers 4 and thumb 5. The handle of the spoon 6 is shown more clearly in other views.

The elongated device 2 is designed to be adjustable so that it can be suitably fitted around the hand 1 of various sizes. When a compression flat 9 is pushed toward the hand 1, an adjustment spring 10 pulls the first end and the second end of the elongated device 2 together to fit firmly around the hand 1. This will be further shown in greater detail in FIGS. 6, 7, and 8.

Figure 2:
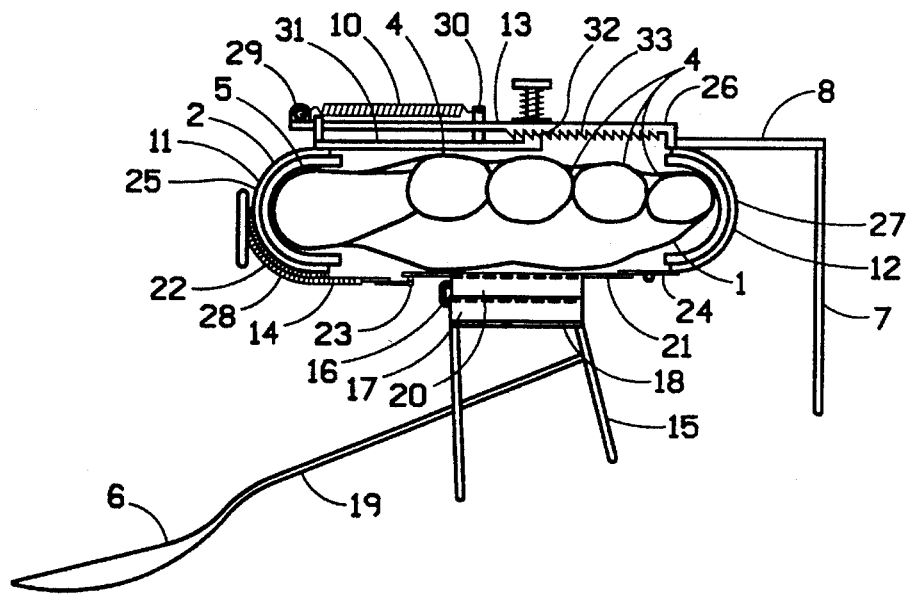
FIG. 2 is a section elevation of a hand in the device as taken through FIG. 1.

Referring to FIG. 2 there is shown an elevation view of the elongated device 2 disposed on the hand 1. The fingers 4, hand 1, and thumb 5 are shown firmly held between a first end 11 and a second end 12 a third end 13, and a fourth end 14 of the elongated device 2. An end stand 7 is shown suitably fixed to the second end 12 of the elongated device 2 by a column rod 8.

The adjustment spring 10 with a first end and a second end is shown at the third end 13 of the device 2 and the spoon 6 is shown suitably fixed to a utensil and tool stand 15 that is further suitably fixed to the fourth end 14 of the elongated device 2. A prehensile tool hook 16 further shown suitably engaged with a concave foundation plate 17. The prehensile tool hook 16 is also rigidly fixed to a convex foundation plate 18. The convex foundation plate 18 is also shown suitably fixed to the utensil and tool stand 15 which is further suitably fixed to a spoon handle 19.

The concave foundation plate 17 is further fixed to a U-base plate 20 which is further suitably fixed to a clasp bar 21. A first end of the clasp bar 21 is shown with a U-bar 23 suitably fixed to the clasp bar 21. A second end of the clasp bar 21 is shown suitably fixed to a first end of a hinge 24. A second end of the hinge 24 is shown suitably fixed to a second end of a second conformance band 27. A first end of the second conformance band 27 is suitably fixed to a second end of an adjustment bar 26. A first end of the adjustment bar 26 is shown slidably connected near a first end of a first conformance band 25. A first hook and loop latch band 22 is shown suitably attached near a second end of the first conformance band 25 by a second hook and loop band 28 or buttons or snaps or other suitable means not shown. The second hook and loop band 28 has a first end and second end.

A first end of the adjustment spring 10 is shown fixed or suitably connected to an adjustment bar eye 29. A second end of the adjustment spring 10 is also shown suitably attached to a second end of an adjustment nib 30. A first end of the adjustment nib 30 is suitably fixed to a push in bar 31.

A first end of the push-in bar 31 is suitably fixed to the first end of the first conformance band 25. A second end of the push-in bar 31 has a push-in rack 32 that is shown meshed with an adjustment bar rack 33 that if formed in the adjustment bar 26.

The end stand 7 is shown suitably fixed to a second end of the column rod 8. A first end of the column rod 8 is also shown suitably fixed to the second end of the adjustment bar 26 and the second end of the second conformance band 27.

Referring to FIG. 3 there is shown an elevation view of the elongated device 2 and how it could be suitably attached to a knife 34.

The knife 34 is comprised of a blade 35 suitably fixed to a convex foundation plate 36 and a first hook and loop pad 37 suitably fixed to the convex foundation plate 36 by adhesive, screws or snaps not shown.

The knife 34 is used to cut meat, or other food or material by moving the elongated device 2 in a rocking like motion 38. As the blade 35 moves in the rocking like motion 38 and is pressed a downward direction 39 and cuts whatever is below the blade 35.

Referring to FIG. 4 there is shown the elongated device 2 as it would be used to hold and support a cup 40.

The cup 40 would have a second hook and loop pad 41 not shown in this figure and a second prehensile tool hook 42. The second prehensile tool hook 42 hooks around a concave foundation plate 17 that is suitably fixed to and is pan of the elongated device 2. When the cup 40 is filled with a liquid or some other material the prehensile tool hook 42 prevents the cup 40 from pulling away from the elongated device 2 and further prevents the cup 40 from falling downward 39. The hook and loop pad 41 further prevents the cup 40 from moving laterally.

Referring to FIG. 5 there is shown another elevation of the elongated device 2 and the cup 40 as taken from FIG. 4.

This elevation is shown to add clarity to the means of the elongated device 2 holding the cup 40.

Figure 6:
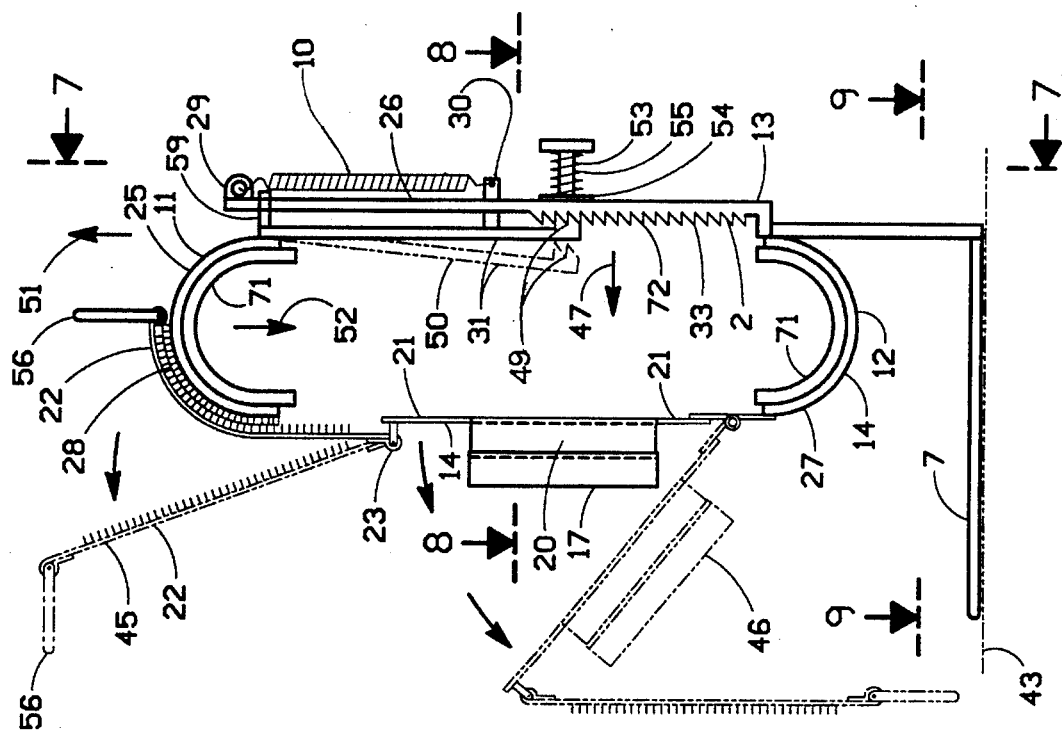
FIG. 6 is an enlarged elevation view of the device.

Referring to FIG. 6 there is shown an enlarged elevation of the elongated device 2 as it would stand on a table surface 43, or counter, or other surface prior to use or after use.

The elongated device 2 would be set on the table surface 43 on the end stand 7 to facilitate the placement of the hand in the elongated device 2 or removing the hand from the elongated device 2.

The elongated device 2 is shown with the first end 11, the second end 12, the third end 13 and the fourth end 14. At the first end 11 of the elongated device 2 there is shown the first conformance band 25 with a first end and a second end and the first conformance band 25 is made of a semi-rigid material such as aluminum, plastic or some other suitable material that will bend or flex to suit the configuration of a particular hand. The second hook and loop band 28 is shown suitably fixed near the second end of the first conformance band 25 by adhesive or other suitable means.

The first hook and loop latch band 22 with a first side, a second side, a first end and a second end has a pull ring 56 suitably fixed to the first end and hook and loop in the first side. The second end of the hook and loop latch band 22 is shown suitably fixed to the U-bar 23. The U-bar 23 is shown suitably fixed to the first end of the clasp bar 21 and the second end of the clasp bar 21 is shown suitably fixed to the first end of the hinge 24. The clasp bar 21 is on the fourth end 14 of the elongated device 2. The hinge 24 bends to allow the clasp bar 21 to rotate open or closed. The second end of the hinge 24 is shown suitably fixed to the second conformance band 27 that is located at the fourth end 14 of the elongated device 2 and is similar to the first conformance band 25. The second end of the second conformance band 27 is shown suitably fixed to the second end of the adjustment bar 26.

The adjustment bar 26 has a first end and a second end and a first side and a second side. The first end of the adjustment bar 26 is shown suitably fixed to the second end of the second conformance band 27 on the third end 13 of said elongated device 2 near the fourth end 14 of said elongated device 2 and extends near the first conformance band 25 at the first end 11 of the elongated device 2.

The adjustment bar eye 29 is shown suitably fixed to the second end of the adjustment bar 26 and on the first side of the adjustment bar 26. The adjustment bar rack 33 is shown on the second side and near the first end of the adjustment bar 26.

The adjustment bar eye 29 is shown with a first end and a second end with the second end of the adjustment bar eye 29 suitably fixed near the second end of the adjustment bar 26. A hole is formed near the second end of the adjustment bar eye 29.

The push-in bar 31 has a first end and a second end and a first side and a second side. The push-in bar 31 has push-in rack 322 with push in gear teeth 49 near the second end and the first side of the push-in bar 31. The second end of the push-in bar 31 is shown suitably fixed to the first end of the first conformance band 25.

The adjustment nib 30 is shown with a first end and a second end. The first end of the adjustment nib 30 is shown suitably fixed to the second side of the push-in bar 31 near the first end of the push-in bar 31 and extends through the adjustment bar 26. The second end of the adjustment nib 30 has a hole formed in it to receive the adjustment spring 10.

The adjustment spring 10 had a first end and a second end. The first end of the adjustment spring is shown inserted into the hole formed in the adjustment bar eye 29 and further suitably fixed to the adjustment bar eye 29. The second end of the adjustment spring 10 is shown inserted into the hole formed in the second end of the adjustment nib 30 and further fixed to the second end of the adjustment nib 30.

A compression rod 55 is shown with a first end and a second end. The first end of the compression rod 55 is shown suitably fixed to the second side of the push-in bar 31 at the push-bar in rack 32. The compression rod 55 extends through a slot formed in the adjustment bar 26 and a compression washer 54 on the second side of the adjustment bar 26. The second end of the compression rod 55 is fixed to the first side of the compression flat 9. The second side of the compression flat 9 is where a thumb or finger touches and pushes the compression flat 9.

A compression spring 53 is shown suitably wound around the compression rod 55 to suitably force the compression rod 55 and the compression flat 9 to thrust the push-in rack 32 teeth 49 to suitably mesh with the adjustment bar rack 33 gear teeth 72.

Prior to placing the hand in the elongated device 2, the first hook and loop latch band 22 with hook and loop suitably attached to the inside of the first hook and loop latch band 22, is pulled away from the second hook and loop band 28 fixed to the second end of the first conformance band 25, as shown in position B 45, allowing the hinge 24 to rotate open to position C 46. The compression flat 9 is further compressed in a depressed direction 47 further pushing out on the push in rack 32 further disengaging the adjustment bar rack 33 from the push-in rack 32 as shown in position D 50. The first end 11 of the elongated device 2 can then be moved up in direction 51 or down in direction 52 to be adjusted to suit the size of the hand or fingers on which the elongate device 2 is to be placed. When the compression flat 9 is thrust inward in a depressed direction 47 a compression spring 53 is compressed against a compression washer 54 with a top side and bottom side. When the thumb or finger is removed from the compression flat 9, the compression spring 53 thrusts against the inside of the compression flat 9 and the top side of the compression washer 54 thus thrusting the compression flat 9 away from the compression washer 54 which further causes the compression rod 55 that is suitably fixed to the push-in bar 31 to pull the push-in bar gear teeth 49 further forcing the push-in bar gear teeth 49 to mesh with the adjustment bar rack 33. One of two adjustment guides 58 is shown suitably fixed to the push down bar 31 and allow the adjustment bar 26 to slide toward the first end 11 or the second end 12 of the elongated device 2.

The first end of the adjustment spring 10 is shown suitably fixed to the adjustment bar eye 29 and the second end of the adjustment spring 10 is shown suitably fixed to the adjustment nib 30.

The adjustment spring 10 allows the first end 11 of the elongated device 2 to be pulled away from the second end 12 of the elongated device 2 thus expanding the elongated device 2 for a larger hand. When the first end 11 of the elongated device 2 is compressed or pushed down, the slope on the first side of the adjustment bar rack 33 or adjustment rack gear teeth 72 push against the slope on the second side of the push-in bar gear teeth 49 thus disengaging the gear teeth from each other and allowing the first end 11 of the elongated device 2 to be pushed toward the second end 12 of the elongated device 2 thus compressing the elongated device 2 onto a smaller hand or fingers. When the elongated device 2 is suitably compressed, the compression spring 53 again forces the push-in bar gear teeth 49 to mesh with the adjustment rack gear teeth 72 until the second side or perpendicular side of the adjustment bar gear teeth 72 mesh and lock with the first side of the push-in bar gear teeth 49 to where the first end 11 of the elongated device 2 cannot be moved away from the second end 12 of the elongated device 2.

The U-base plate 20 is shown suitably fixed to the clasp bar 21. The U base plate 20 has a first side, a second side, a third side and a fourth side, a first end and a second end. The second side of the U-base plate 20 is shown suitably fixed to the clasp bar 21. The first end of the U-base plate 20 is near the U-bar 23 and the second end of the U-base plate 20 is near the hinge 24.

The concave foundation plate 17 having a rectangular or square configuration has a first side, a second side, and a first end, and a second end. The first side of the concave foundation plate 17 is suitably fixed to the U-base plate 20. The second side of the concave foundation plate 17 has a first hook and loop pad suitably fixed to it.

Soft pads 71 are made out of rubber or other suitable material that will protect the hand, fingers or thumb from injury are suitably fixed in the first end 11 and the second end 12 of the elongated device 2.

Figure 7:
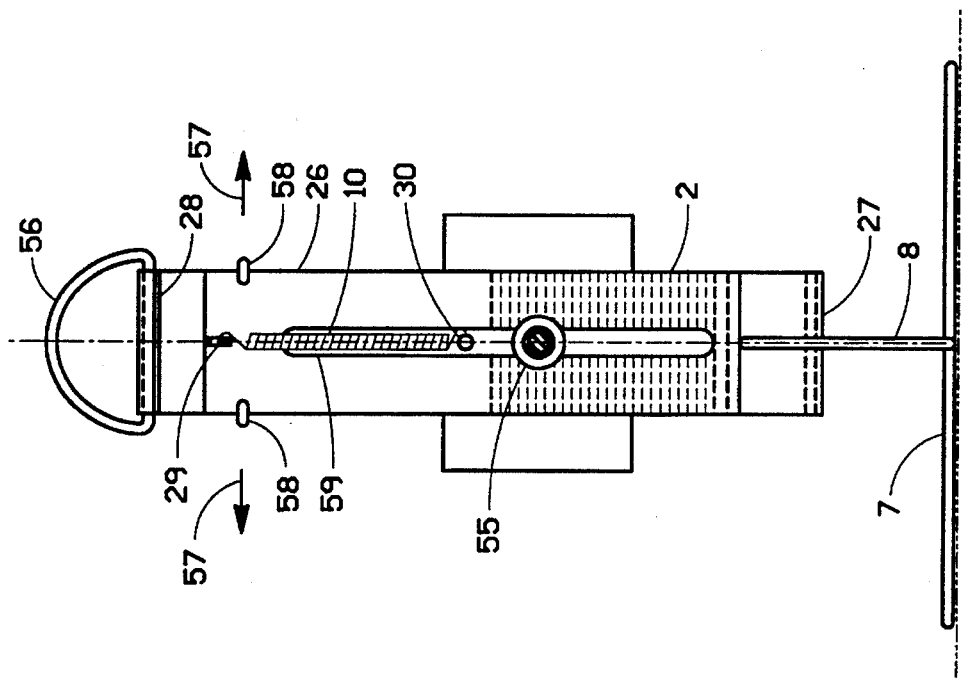
FIG. 7 is another elevation view of the device.

Referring to FIG. 7 there is shown another elevation of the elongated device 2.

The pull ring 56 is shown suitably fastened to the first end of the second hook and loop band 28.

The adjustment bar 26 is shown held in place and prevented from moving laterally 57 by the two adjustment guides 58. The two adjustment guides 58 are rigidly fixed to the push-in bar and allow the adjustment bar 26 to move in the direction of the first end 11 of the elongated device 2 or in the direction of the second end 12 of the elongated device 2.

The adjustment spring 10 is shown suitably fixed to the adjustment bar eye 29 at the first end of the adjustment spring 10 and it is further shown suitably fixed at the second end to the adjustment nib 30. To allow the adjustment bar 26 to move relative to the adjustment nib 30, an adjustment slot 59 with a first end and a second end is shown formed in the adjustment bar 26. The first end of the adjustment slot 59 is near the first end 11 of the elongated device 2 and the second end of the adjustment slot 59 is near the second end 12 of the elongated device 2. The compression rod 55 is behind the compression flat and is fixed to the first side of the push-in bar and extends through the adjustment slot 59 where it is suitably fixed to the compression flat.

The end stand 7 and the column rod 8 are shown suitably fixed to the second conformance band 27 and the adjustment bar 26.

Figure 8:
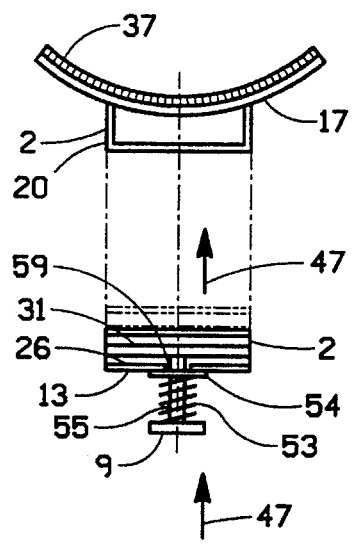
FIG. 8 is a section view of the device as taken through FIG. 6.

Referring FIG. 8 there is shown a section view of the elongated device 2 as taken through FIG. 6.

The compression flat 9 is shown suitably fixed to the compression rod 55 that further extends through the adjustment slot 59 formed in the adjustment bar 26 where it is suitably fixed to the push-in bar 31 and push-in bar gear teeth. The compression spring 53 is shown disposed between the second side of the compression flat 9 and the top side of the compression washer 54. The bottom side of the compression washer 54 is shown resting on the first side of the adjustment bar 26. When the compression flat 9 is pushed it further pushes the push-in bar 31 in a depressed direction 47 thus disengaging the gears.

On the third end 13 of the elongated device 2 there is shown a section view of the concave foundation plate 17 and the U base plate 20 that is suitably fixed to the concave foundation plate 17. A first hook and loop pad 37 is shown fixed to the concave foundation plate 17.

Figure 9:
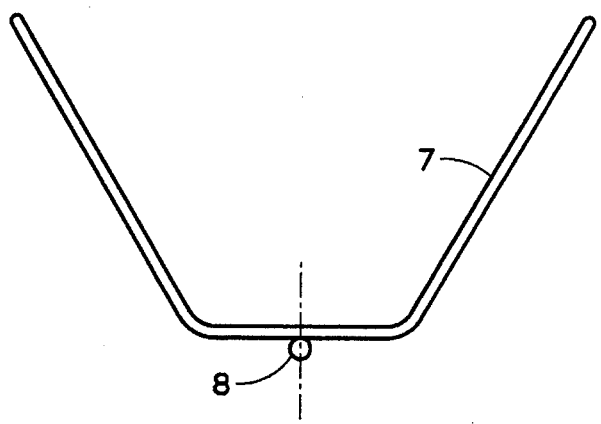
FIG. 9 is another section view as taken through FIG. 6.

Referring to FIG. 9 there is shown a section view of the end stand 7 and the column rod 8 as taken through FIG. 6.

The column rod 8 with a first end and a second end is shown suitably fixed to the end stand 7 at the second end of the column rod 8 by means of welding or adhesive or other suitable means by design choice. The end stand 7 is shown in the configuration of a U, however, it could be circular, rectangular, or V shaped by design choice. The first end of the column rod 8 is suitably fixed to the second conformance band and the adjustment bar.

Figure 10:
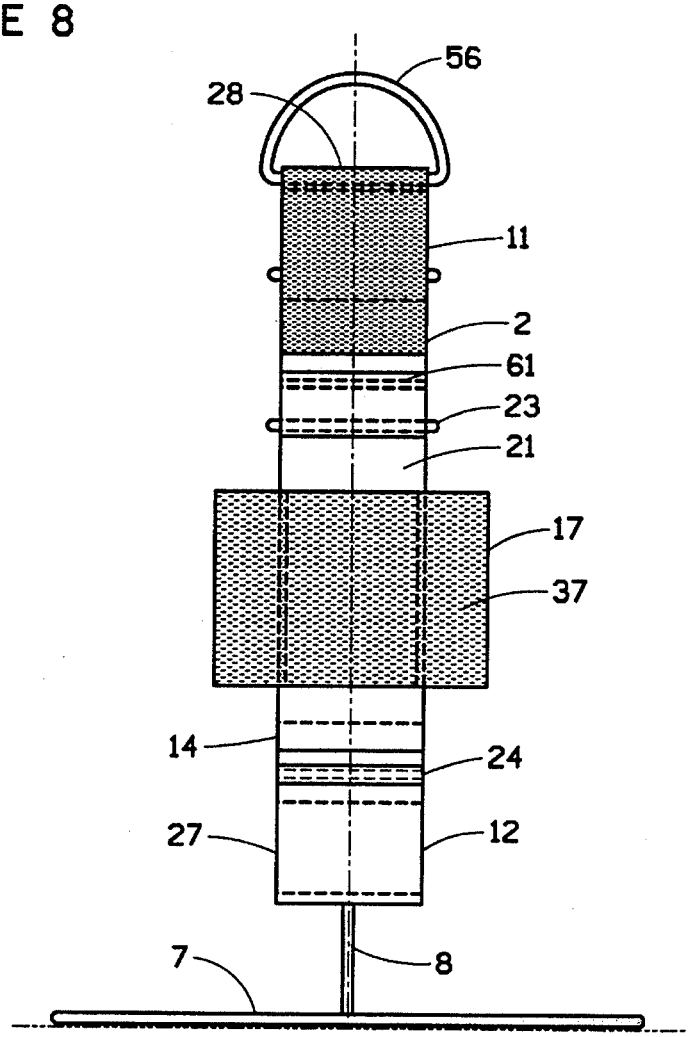
FIG. 10 is another elevation view of the device.

Referring to FIG. 10 there is shown an elevation view of the forth end 14 of the elongated device 2. The pull ring 56 is shown at the first end 11 of the elongated device 2.

The pull ring 56 is shown suitably fixed to the first end of the second hook and loop band 28. The second end of the second hook and loop band 28 is shown suitably fixed to the U-bar 23 that is further suitably fixed to the clasp bar 21. The second hook and loop band 28 is wrapped around the U-bar 23 and is further held together by stitches 61 or by adhesive or by any other suitable means by design choice.

The concave foundation plate 17 has a first side and a second side. The first hook and loop pad 37 is shown suitably fixed to the second side of the concave foundation plate 17. The first side of the concave foundation plate 17 is suitably fixed to the clasp bar 21 which is further fixed to the hinge 24 near the second end 12 of the elongated device 2. The hinge 24 is shown fixed to the second conformance band 27. The column rod 8 is shown fixed to the end stand 7.

Figure 11:
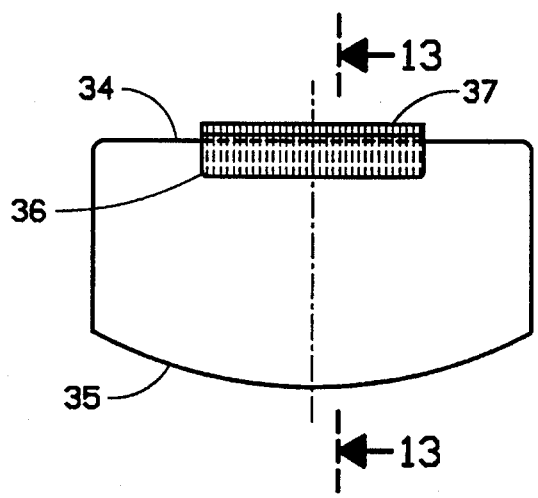
FIG. 11 is an elevation view of the knife.

Referring to FIG. 11 there is shown an elevation of the knife 34.

The convex foundation plate 36 has a first side and a second side. The blade 35 is shown with the first end suitably fixed to second side of the convex foundation plate 36. A second hook and loop pad 37 is shown further shown suitably fixed to the first side of the convex foundation plate 36. The second end of the blade 35 is rounded to allow the blade 35 to be rolled over the food or material to be cut.

Figure 12:
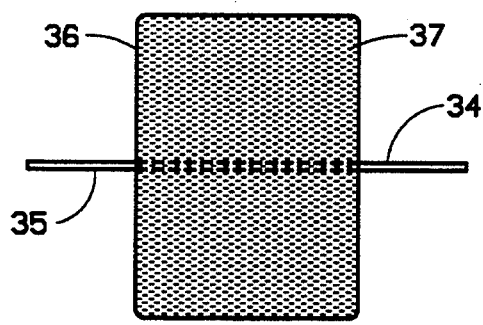
FIG. 12 is a plan view of the knife.

Referring to FIG. 12 there is shown a plan view of the knife 34. The second hook and loop pad 37 is shown suitably fixed to the convex foundation plate 36 which is suitably fastened to the blade 35.

Figure 13:
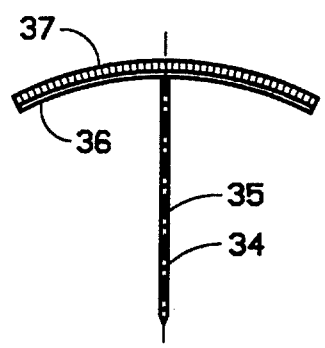
FIG. 13 is a section elevation of the knife as taken through FIG. 11.

Referring to FIG. 13 there is shown a section view as taken through FIG. 11.

The second hook and loop pad 37 is shown suitably fixed to the first side of the convex foundation plate 36. The second side of the convex foundation plate 36 is shown suitably fixed to the first end of the blade 35 of the knife 34.

Figure 14:
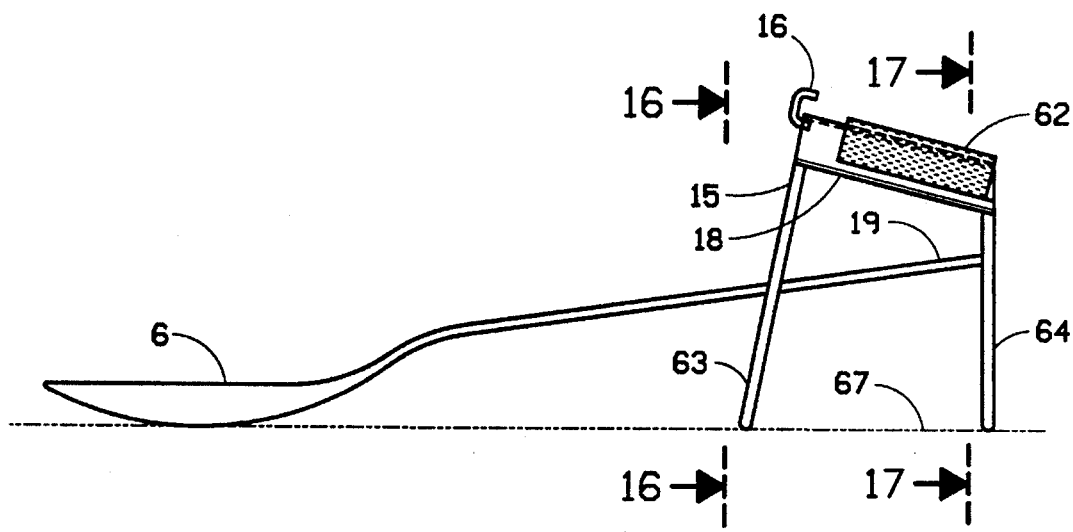
FIG. 14 is an elevation view of a spoon utensil and tool stand and the prehensile tool hook.

Referring to FIG 14 there is shown a side elevation of the spoon 6 suitably fixed to the utensil and tool stand 15. Although a spoon 6 is shown this could also be a fork, knife, screw driver, wrench, hammer, pen, pencil, key, frying pan, ruler or any other tool that is normally held in one hand. The spoon handle 19 is shown fixed to the utensil and tool stand 15.

The prehensile tool hook 16 with a first end and a second end is shown forming essentially a V or U in configuration. The first end of the prehensile tool hook 16 is shown at the upper end extending into space. The convex foundation plate 18 has a lower side and an upper side and a first end and a second end. The second end of the prehensile tool hook 16 is shown suitably fixed to the lower side of the convex foundation plate 18 at the first end of the convex foundation plate 18 by means of welding or adhesive or other suitable means. A second hook and loop pad 62 is shown suitably fixed to the upper side of the convex foundation plate 18.

The first leg 63 with a first end and a second end and the second leg 64 with a first end and a second end are shown suitably fixed to the second end of the convex foundation plate 18 and extend to a table top 67. The first leg 63 is longer than the second leg 64 to allow the convex foundation plate 18 to remain at an angle relative to the table top 67.

Figure 15:
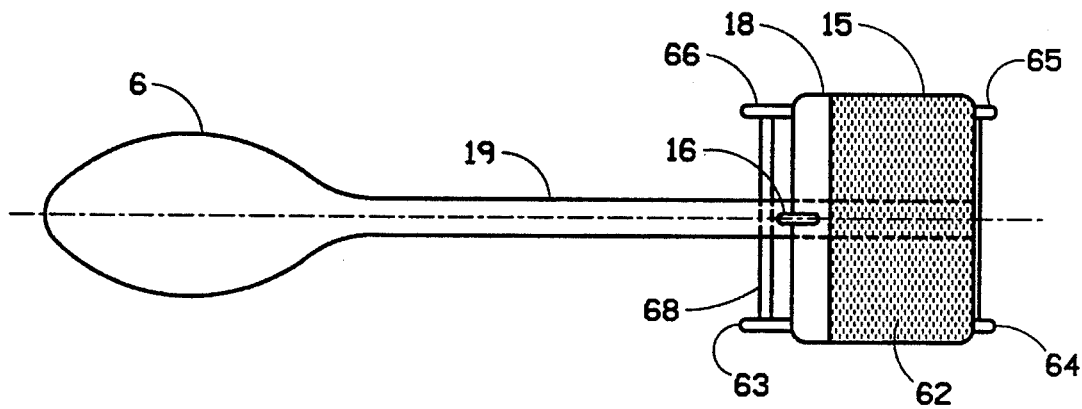
FIG. 15 is a plan view of the spoon utensil and tool stand and the prehensile tool hook.

Referring to FIG. 15 there is shown a plan view of the utensil and tool stand 15 suitably fixed to a spoon 6. The first end of the spoon 6 is the bowl end and the second end of the spoon is the spoon handle 19.

The utensil and tool stand 15 has a first leg 63, a second leg 64, a third leg 65, and a fourth leg 66, all with a first end and a second end, that are fixed to the lower side of the convex foundation plate 18 at the first end of each leg. A second hook and loop pad 62 is shown suitably fixed to upper side of the convex foundation plate 18. The prehensile tool hook 16 is shown at the first end of the convex foundation plate 18. A first cross bar 68 with a first end and a second end is shown suitably fixed at the first end to the first leg 63 and at the second end to the fourth leg 66.

Figure 16:
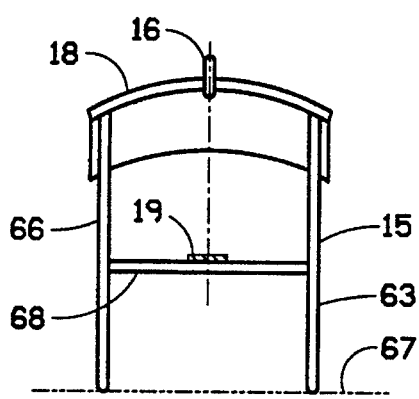
FIG. 16 is a section elevation as taken through FIG. 14.

Referring to FIG. 16 there is shown a section elevation of the utensil and tool stand 15 as taken through FIG. 14.

The spoon handle 19 is shown supported and suitably fixed to the first cross bar 68. The first cross bar 68 is shown suitably fixed to the fourth leg 66 at the first end of the first cross bar 68 and extends to the first leg 63 at the second end of the first cross bar 68 where it is further suitably fixed to the first leg 63. The fourth leg 66 and the first leg 63 are shown suitably fixed to the lower side and first end of the convex foundation plate 18. The prehensile tool hook 16 is shown fixed near the center and first end of the convex foundation plate 18. The first leg 63 and the fourth leg 66 are shown resting on the table top 67.

Figure 17:
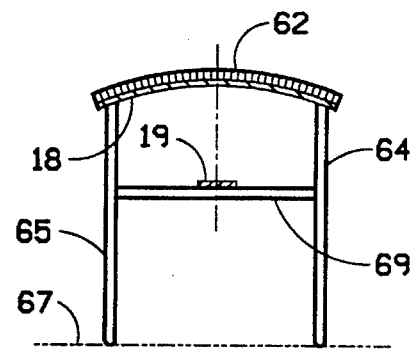
FIG. 17 is another section elevation as taken through FIG. 14.

Referring to FIG 17 there is shown another section elevation as taken through FIG. 14.

The second end of the spoon handle 19 is shown suitably fixed to the second cross bar 69. The second cross bar 69 has a first end and a second end. The first end of the second cross bar 69 is suitably fixed to the third leg 65 and the second end of the second cross bar 69 extends to the second leg 64 where it is suitably fixed to the second leg 64.

The first end of the second leg 64 and the third leg 65 are suitably fixed to the lower side of the convex foundation plate 18. The second end of the second leg 64 and the third leg 65 are shown resting on the table top 67.

A second hook and loop pad 62 with a first side and a second side is shown suitably fixed to the top side of the convex foundation plate 18.

Figure 18:
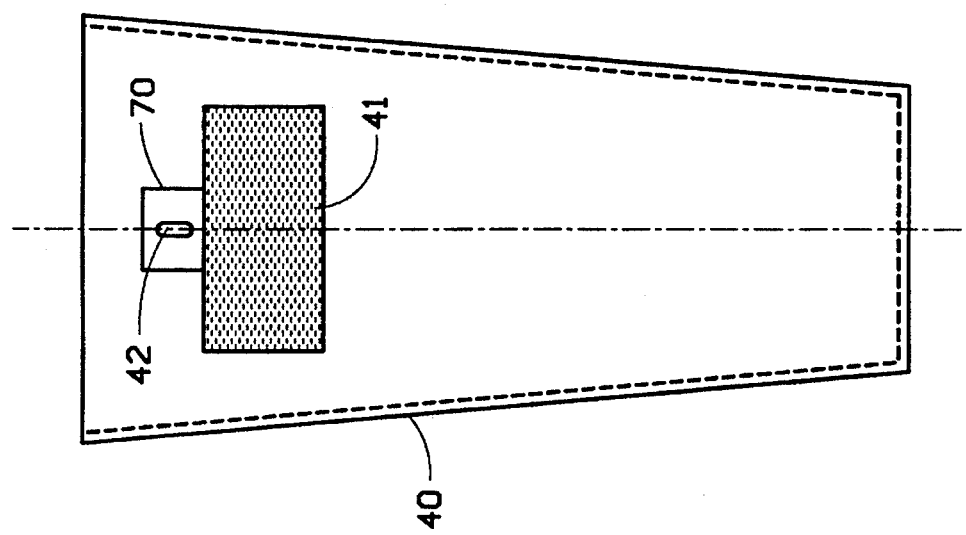
FIG. 18 is an elevation of a cup with a prehensile tool hook fixed to the cup.

Referring to FIG. 18 there is shown a cup 40 with a hook and loop pad 41 suitably fixed to the cup 40 by adhesive or other suitable means a prehensile tool hook 42 is shown suitably fixed to the prehensile tool hook base plate 70 that is further fixed to the cup 40 by adhesive or other suitable means.

Figure 19:
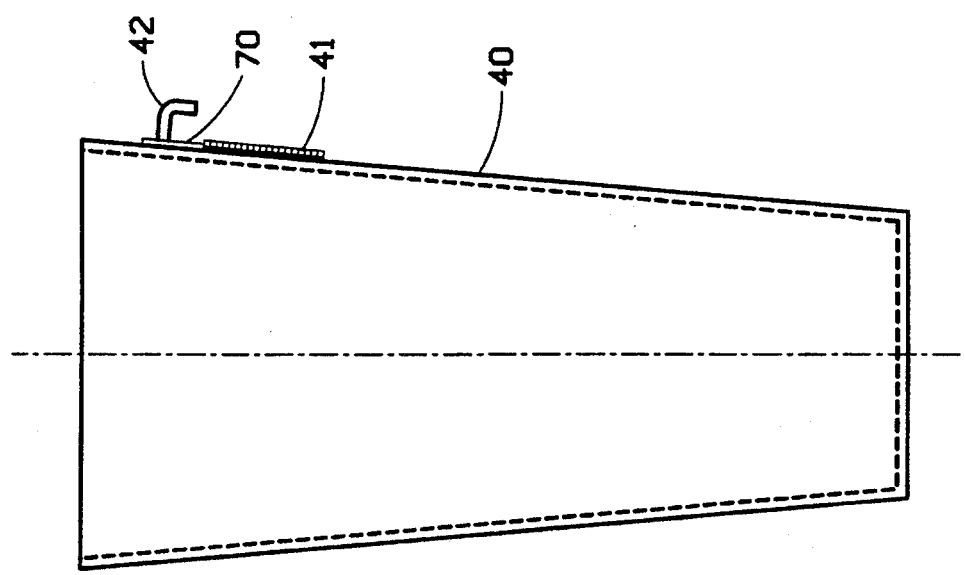
FIG 19 is a side elevation of the cup with the prehensile tool hook fixed to the cup.

Referring to FIG. 19 there is shown an elevation view taken at ninety degrees to FIG. 18.

The prehensile tool hook 42 is shown suitably fixed to the prehensile tool hook base plate 70. The prehensile tool hook base plate 70 is further shown suitably fixed to the cup 40. The hook and loop pad 41 is shown suitably fixed to the outside of the cup 40 near the upper end of the cup.

Although the system described in detail supra has been found to be most satisfactory and preferred, many variations are possible. For example; the elongated device 2 can be made for three fingers, the stand can be made round, snaps can be used instead of velcro.

Although the invention has been described with reference to the preferred embodiment it will be understood by those skilled in the art that additions, modifications, substitutions, deletions and other changes not specifically described may be made in the embodiments herein, it should be understood that the details herein are to be interpreted as illustrative and are not in a limiting sense.

What is claimed as invention is:

1. A prosthetic device for enabling a person with a disabled hand or other upper extremity to use utensils and tools comprising:

a substantially elongated semi-rigid band having compression adjustment means, securing means, and guide means, said elongated band having first and second ends, said first and second ends defining curved members;

said compression adjustment means including an adjustment spring, meshing ratchet teeth having two separate sets of rachet teeth, and a compression pin having a compression spring, said adjustment spring rigidly attached to said first end and to said first set of rachet teeth which engage said second set of rachet teeth, said second set of rachet teeth attache to said second end, said compression pin being rigidly attached to said first set of rachet teeth to disengage upon depression of said compression pin, said compression spring being disposed around said compression pin for returning said compression pin to original position;

said securing means including a hook and loop fastener, an attachment bar and a hinge for allowing said elongated band to remain secured at a predetermined size set by said adjustment means, said hinge attached to said first end, said hook and loop fastener attached to said second end, said attachment bar located there between for attaching said utensils or tools to said elongated band, said hinge for allowing said attachment bar to pivot to an open position for insertion of said hand or other upper extremity;

said guide means comprising an elongated slot in each of said elongated band and said second set of rachet teeth for guiding said adjustment spring and compression pin along a line parallel to edges of said elongated band.

2. A prosthetic device of claim 1 where in said elongated band further comprises a column rod and an end stand, said column rod having one end rigidly attached to said second set of rachet teeth and a second end terminating in an end stand, said end stand having an upper support surface and a plurality of legs, said plurality of legs adapted to support the device on a flat surface.

* * * * *